(12) United States Patent  
Amirouche et al.

(10) Patent No.: US 9,125,749 B2
(45) Date of Patent: Sep. 8, 2015

(54) PATELLAR IMPLANT WITH VARIABLE WEIGHTS FOR KNEE REPAIR SURGERY

(76) Inventors: Farid Amirouche, Highland Park, IL (US); Mark H. Gonzalez, Chicago, IL (US); Wayne Goldstein, Highland Park, IL (US)

( * ) Notice: Subject to any disclaimer, the term of this patent is extended or adjusted under 35 U.S.C. 154(b) by 398 days.

(21) Appl. No.: 12/910,597

(22) Filed: Oct. 22, 2010

(65) Prior Publication Data

US 2012/0101584 A1    Apr. 26, 2012

(51) Int. Cl.
A61F 2/38 (2006.01)
A61B 17/17 (2006.01)
A61F 2/46 (2006.01)
A61F 2/30 (2006.01)

(52) U.S. Cl.
CPC ........... *A61F 2/3877* (2013.01); *A61B 17/1767* (2013.01); *A61F 2/4684* (2013.01); *A61F 2002/30317* (2013.01); *A61F 2002/30319* (2013.01); *A61F 2002/30604* (2013.01); *A61F 2002/30616* (2013.01); *A61F 2002/30892* (2013.01)

(58) Field of Classification Search
CPC ............. A61F 2/3877; A61F 2002/30892
USPC .............................. 623/20.18, 20.2
See application file for complete search history.

(56) References Cited

U.S. PATENT DOCUMENTS

| 5,019,104 | A  | * | 5/1991  | Whiteside et al. ........... 623/20.2 |
| 5,314,480 | A  | * | 5/1994  | Elloy et al. ................. 623/20.2 |
| 5,769,856 | A  |   | 6/1998  | Dong et al. |
| 6,146,423 | A  |   | 11/2000 | Cohen et al. |
| 6,589,248 | B1 | * | 7/2003  | Hughes ......................... 606/102 |
| 6,616,696 | B1 |   | 9/2003  | Merchant |
| 6,855,150 | B1 |   | 2/2005  | Linchan |
| 2004/0236428 | A1 | * | 11/2004 | Burkinshaw et al. ...... 623/20.15 |
| 2007/0265708 | A1 | * | 11/2007 | Brown et al. ................ 623/20.2 |

* cited by examiner

*Primary Examiner* — Bruce E Snow
*Assistant Examiner* — Melissa Hoban
(74) *Attorney, Agent, or Firm* — Brinks Gilson & Lione

(57) ABSTRACT

The present disclosure relates to a device for repairing a patient patella. The device comprises a patellar trial piece and a patellar implant. The patellar trial piece has selectable variable weights to correct mechanical properties of the patient patella. Such mechanical properties to be corrected include a moment of inertia and/or a center of gravity of the patient patella. The patellar implant has embedded weights correspond to the variable weights of the patellar trial piece. In one embodiment, the patellar trial piece has a plurality of variable weights to be inserted into a plurality of holes in the patellar trial piece. The weights are made of different materials. In another embodiment, the patellar trial piece has a rounded top surface and a substantially flat bottom surface with a plurality of pegs. The pegs are selected from pegs with variable weights that are made of different materials.

12 Claims, 5 Drawing Sheets

PATELLAR IMPLANT WITH VARIABLE WEIGHTS FOR KNEE REPAIR SURGERY

BACKGROUND

1. Field of the Disclosure

The disclosure relates to joint replacement, and more particularly, to systems and methods for selecting a patellar implant using a patellar trial piece with variable weights.

2. Related Technology

Joint replacement is becoming increasingly widespread recently. One of the most widely practiced joint replacements is the knee joint replacement. In many cases, the replacement of the knee joint with a prosthetic also involves the replacement of a portion of the patella with an artificial patellar implant.

However, in a significant percentage of the cases, the patellar implant typically fails after five to fifteen years due to instable patellar implant. A failing patella could lead to significant pain in the patient and typically requires a second operation to replace the failed patellar implant.

A patellar trial with different size, thickness, shape or material during a knee replacement surgery is known. However, the current patellar trial lacks the matching of mechanical properties, mass and material accuracies which are crucial to the stability and longevity of the repaired patella after the knee replacement surgery.

SUMMARY

A device for repairing a patient patella, the device comprising a patellar trial piece and a patellar implant. The patellar trial piece has selectable variable weights to correct mechanical properties of the patient patella. Such mechanical properties to be corrected include, patella tracking and alignment, mass, moment of inertia and/or a center of gravity of the patient patella. The patellar implant has embedded or added weights, which correspond to the variable weights of the patellar trial piece. The trail piece allows for selection of an equivalent weighted patella sterilized to be selected for the patient artificial knee implant.

In one embodiment, the patellar trial piece has a plurality of variable weights to be inserted into a plurality of holes in the patellar trial piece. The weights are made of different materials such as brass, tungsten, stainless steel, or other durable material.

In another embodiment, the patellar trial piece has a rounded top surface and a substantially flat bottom surface with a plurality of pegs. The pegs are selected from pegs with variable weights. The pegs are made of different material such as brass, tungsten, stainless steel, or other durable material. The pegs can either be inserted at pre-drilled locations or simply interchangeable to allow for different selection of weight and pegs length.

A surgeon can use the device to select a patellar implant to maximize the stability and longevity of the repaired patella. The method of selecting the patellar implant for a knee repair surgery comprises three steps. The first step is selecting a size of a patellar trial piece. The second step is selecting weights from a plurality of variable weights to insert into the patellar trial piece such that a predetermined moment of inertia and/or a predetermined center of gravity of a patient patella are obtained, and the integrity of the patient knee-patella is preserved. The third step is selecting a patellar implant based on the selected size and weights of the patellar trial piece. The surgeon will be given a selection of patella with different weights that will conform to the newly resurfaced patella and mathematically determined options of new patella insertion. This will be based on the proposed bone cuts and thickness as well as the surgical procedure undertaken to achieve the patient's patella cuts.

Further objects, features and advantages of this disclosure will become readily apparent to persons skilled in the art after a review of the following description, with reference to the drawings and claims that are appended to and form a part of this specification.

BRIEF DESCRIPTION OF THE DRAWINGS

The disclosure can be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

DETAILED DESCRIPTION

The present disclosure is directed to systems and methods for use in knee repair surgery. It will be apparent that the device described herein below, may be applied to a variety of medical procedures, including, but not limited to, joint replacement surgeries performed on the shoulder, elbow, ankle, foot, fingers and spine.

Figure 1:
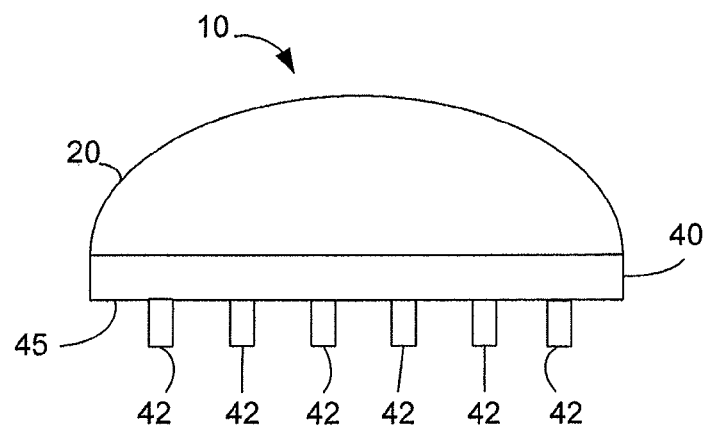
FIG. 1 is a side view of a first embodiment of a patellar trial piece with removable pegs.

FIG. 1 shows a first embodiment of a patellar trail piece 10 in a side view. The patellar trial piece 10 may have different sizes to be selected by a surgeon. The manufacturing process for the patellar trial piece is known in the art. The manner of attaching the pegs, their coating, length, geometry, material may be determined depending on the particular application.

Figure 2:
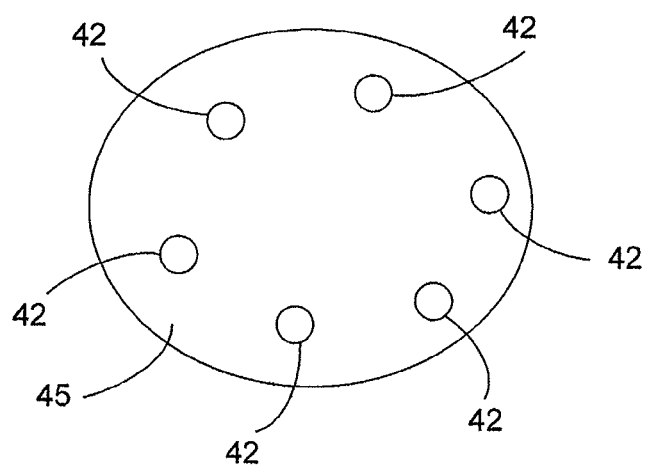
FIG. 2 is a bottom view the patellar trial piece in FIG. 1.

The patellar trial piece 10 comprises two components, an articular surface member 20 and a drill guide 40. The drill guide 40 acts as the base of the articular surface member 20. The drill guide 40 has a bottom surface 45 as shown in both FIG. 1 and FIG. 2. The bottom surface 45 is preferably substantially flat. A plurality of fixation pegs 42 extend outwardly and downwardly from the bottom surface 45. The fixation pegs 42 provide two functions: one is the fixation and anchoring in the patella; and the second to modify the weight, moment of inertia and center of mass. The ultimate goal is better tracking and stability providing enhanced kinematics reducing pain and providing better function for the artificial knee.

The fixation pegs 42 may be made of different materials such as stainless steel, Cobalt chrome, composite materials, brass, and tungsten. The fixation pegs 42 may have the same size with different weight or same weight with different sizes. The fixation pegs 42 in the patellar trial piece are removable during a knee patella resurfacing procedure. The fixation pegs 42 of the patellar trial piece 10 weigh preferably between 5-25 grams. By attaching different fixation pegs 42 to the bottom surface 45, the mechanical properties of the patella can be adjusted and corrected accordingly. For example, at least one of the moment of inertia or center of gravity of the patient patella can be adjusted to predetermined values by fixing different fixation pegs 42 to the bottom surface 45.

The holes for the pegs 42 are preferably pre-drilled holes and the location of the holes will depend on the size and designs of the pegs 42. For example, the system may be configured such that there are two fixed pegs and one removable peg, or all of the pegs may be removable, or some other suited combination of fixed and removable pegs 42. Surgeon should have the options to decide best locations for the number of weights Alternatively, weights can be added that are not fixation pegs. It will be recognized that surgeon should be given the opportunity to modify the parameters, such as the moment of inertia or center of gravity, based on the patient patella conditions and patella tracking and kinematics.

A patellar implant has similar size and weights as the patellar trial piece. The difference between the patellar implant and the patellar trial piece is the fixation pegs 42 are embedded and thus not removable from the patellar implant. The patellar implant may be molded in advance for each possible combination of different fixation pegs 42. Alternatively, the fixation pegs 42 may be fixed to the patellar trial piece during a surgery. In this case, the patellar trial piece is converted to a patellar implant after the fixation pegs 42 being fixed permanently to the bottom surface 45.

Figure 3:
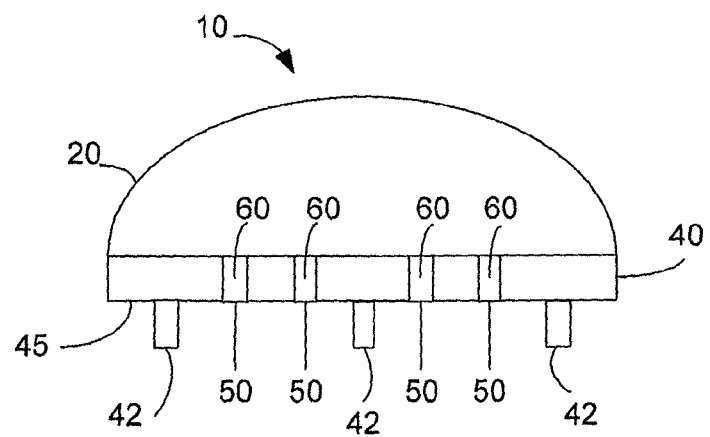
FIG. 3 is a side view of a second embodiment of a patellar trial piece with removable weights.

Referring now to FIG. 3, a second embodiment of a patellar trail piece 10 is shown in a side view. The patellar trial piece 10 comprises two components, an articular surface member 20 and a drill guide 40. The drill guide 40 acts as the base of the articular surface member 20. The drill guide 40 comprises a plurality of holes 50. The drill guide 40 may be made of a suitable metal, such as cobalt chrome. The holes 50 are capable to hold a plurality of weights 60. The weights 60 may be made of different materials such as stainless steel, Cobol chrome, composite materials, brass, and tungsten. The weights 60 in the patellar trial piece are removable, insertable, and interchangeable during a knee patella resurfacing procedure. The removable weights 60 weigh between 5-25 grams. A 25 gram weight would not jeopardize the appearance, the strength, and the stress of the patient patella.

A patellar implant has similar size and weights as the patellar trial piece. In one embodiment, the only difference between them is the weights 60 are embedded and thus not removable from the patellar implant. The patellar implant may be molded in advance for each possible combination of different weights. Or the weights may be embedded and fixed to the patellar trial piece during a surgery using a soldering device. In this case, the patellar trial piece is converted to a patellar implant.

Figure 4:
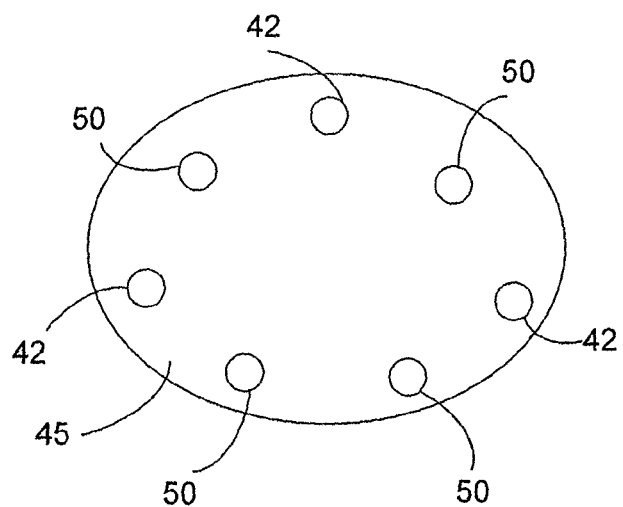
FIG. 4 is a bottom view the patellar trial piece in FIG. 3.
Figure 5:
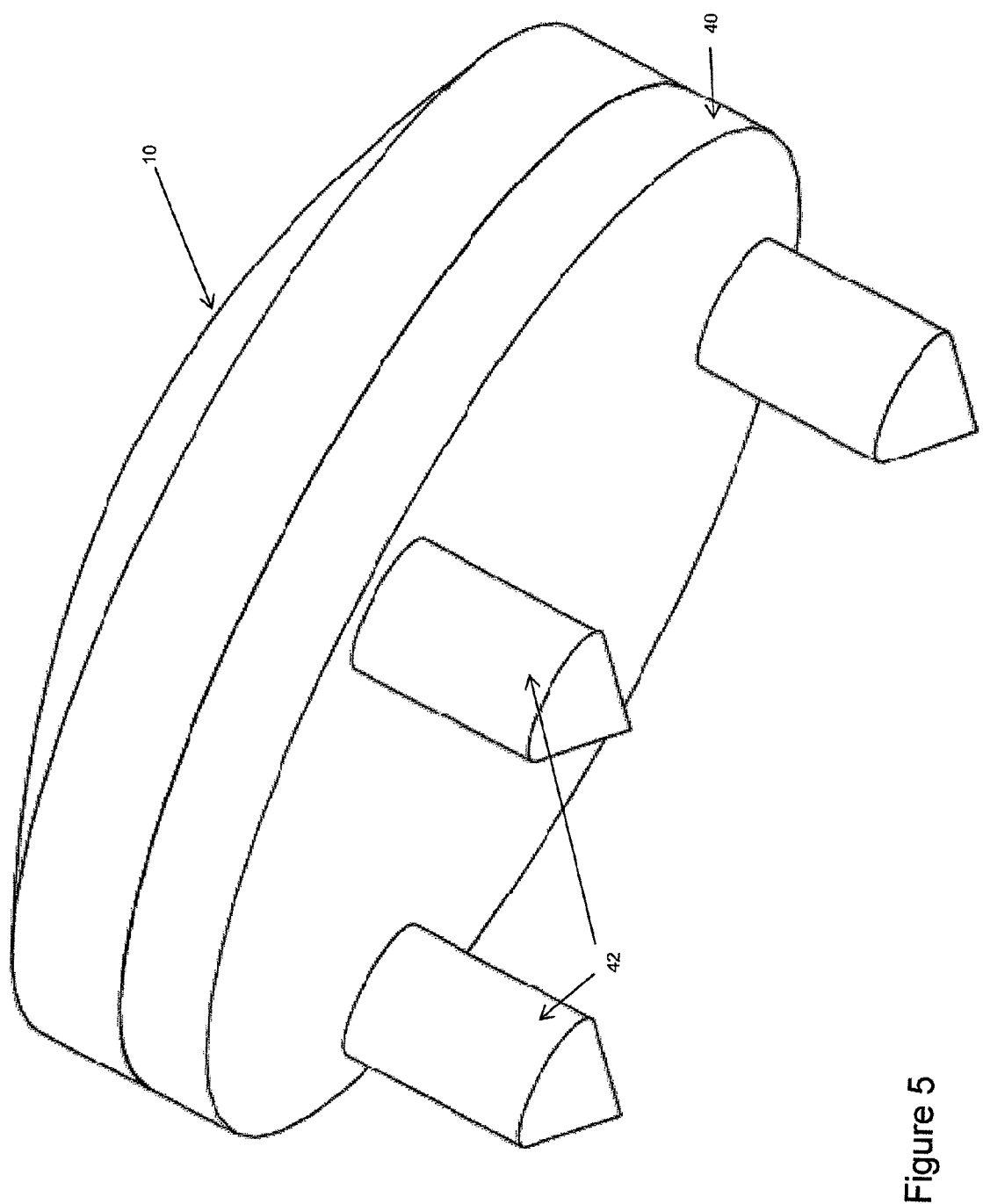
FIG. 5 is a perspective view of the patellar trial piece in FIG. 3.
Figure 6:
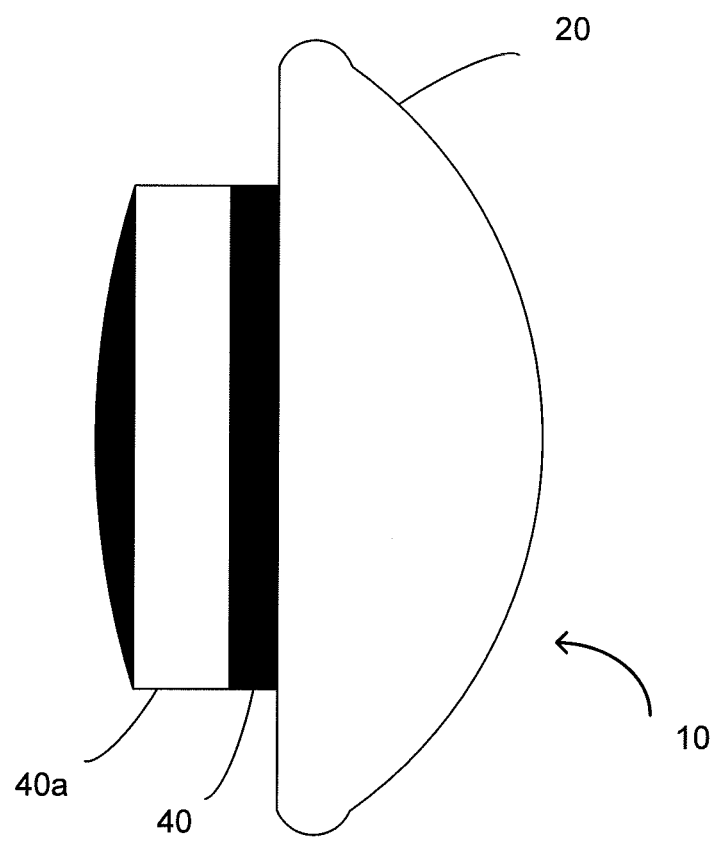
FIG. 6 is a perspective view of an embodiment of a patellar trial piece with removable pegs covered by an enclosure.

Referring to FIG. 3, FIG. 4 and FIG. 5, the drill guide 40 has a bottom surface 45. The bottom surface 45 is substantially flat. A plurality of fixation pegs 42 extend outwardly and downwardly from the bottom surface 45. The fixation pegs 42 may be made of different materials. Referring to FIG. 6 the trial piece 10 includes an enclosure 40a, which may be made of polyethylene.

Figure 7:
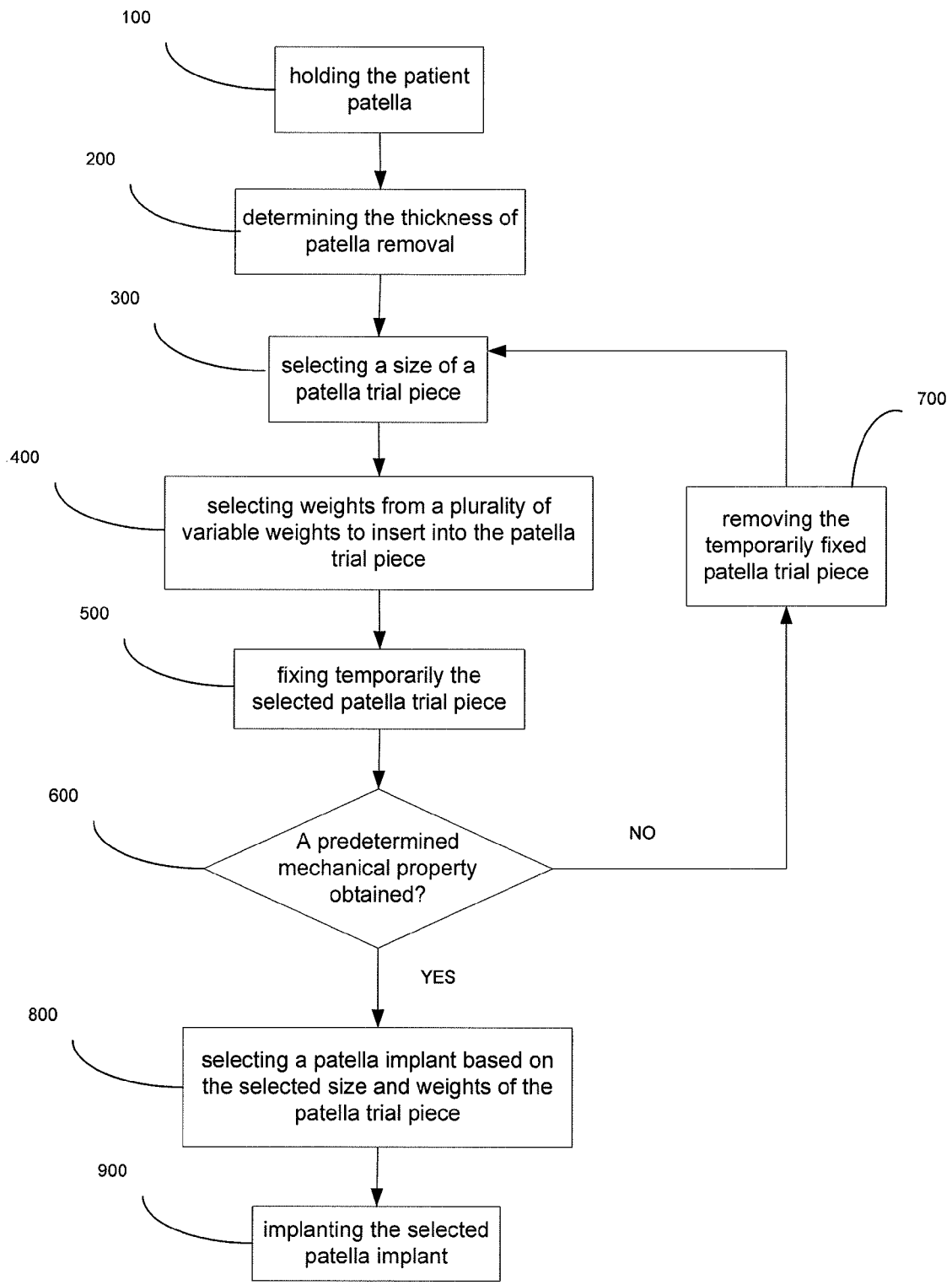
FIG. 7 is a flowchart showing a method of using the patellar trial piece and the patellar implant of the present disclosure.

FIG. 7 is a flowchart showing the method of using the patellar trial piece and the patellar implant of the present disclosure. In step 100, a surgeon first holds the patient patella by a patellar clamp or a patella holder. Then the surgeon determines the thickness of a patella removal through basic measurements of heights and widths at several locations of the patient patella in step 200. The surgeon then shapes the patient natural patella by a surgical saw or other tools. The shaved part of the patella sum is determined mathematically through the measured parameters. In step 300, the surgeon selects a size of a patellar trial piece according to the size of the patella removal. After selecting the size of the patellar trial piece, the surgeon selects weights from a plurality of variable weights to insert into the patellar trial piece in step 400. The surgeon then fixes temporarily the patellar trial piece to a desired position of the patient knee in step 500. If a predetermined mechanical property such as a predetermined moment of inertia (M.O.I) or a predetermined center of gravity (C.G) of a patient patella is obtained in step 600, the surgeon selects a patellar implant based on the selected size and weights of the patellar trial piece in step 800. Otherwise, if the predetermined mechanical property is not obtained, the surgeon removes the temporarily fixed patellar trial piece in step 700 and repeats the steps 300, 400, and 500 until the predetermined mechanical property is obtained. In the final step 900, the surgeon inverts the patellar trial piece and implants the selected patellar implant.

During a knee repair surgery, a surgeon use the above described patellar trial piece and patellar implant to improve patient knee stability, to reduce pain and to increase longevity of the patient knee. The weight of the patellar implant is in accordance with the combined mass of the shaved part. The correct weight and center of gravity provide additional bearing to the patient patella to minimize tilting and any instability during patella motion. The patellar implant with variable weight of the present disclosure delivers maximum stability for maximum longevity and accuracy of the patient patella. Multi-weight zone distribution offers an outstanding weight control along the tracking surface of the femoral component, providing a lower C.G and increased M.O.I that provides a more stable motion during flexion-extension of the knee.

While various embodiments of the disclosure have been described, it will be apparent to those of ordinary skill in the art that many more embodiments and implementations are possible within the scope of the disclosure. Accordingly, the disclosure is not to be restricted except in light of the attached claims and their equivalents.

What is claimed is:

1. A system for repairing a patient patella, the patient patella having a moment of inertia and a center of gravity, the system comprising:
   a plurality of removable and insertable variable weights comprising at least two pegs with different weights from each other; a patellar trial piece comprising an articular surface member, a drill guide, and an enclosure attached to a bottom surface of the drill guide, the patellar trial piece and the variable weights configured to be attached together through the drill guide, the enclosure configured to cover the attached variable weights, and the patellar trial piece configurable to correct at least one of the moment of inertia and the center of gravity of the trial piece to correspond to that of the patient patella to achieve optimal tracking and full range of motion; and a patellar implant with embedded weights, wherein the embedded weights correspond to the at least one of the variable weights.

2. The system of claim 1 wherein each of the variable weights weighs between 5 to 25 grams.

3. The system of claim 1 wherein the variable weights are made of different materials.

4. The system of claim 1 wherein the system comprises a plurality of patellar trial pieces of variable sizes.

5. A device for repairing a patient patella, the patient patella having a moment of inertia and a center of gravity, the device comprising:

a plurality of pegs comprising at least two pegs with different weights from each other; and a patellar trial piece comprising an articular surface member, a drill guide, and an enclosure attached to a bottom surface of the drill guide, the patellar trial piece and the pegs configured to be attached together through the drill guide, the enclosure configured to cover the attached pegs and the patellar trial piece configurable to correct at least one of the moment of inertia and the center of gravity of the trial piece to correspond to that of the patient patella, wherein the plurality of pegs are fixedly insertable in and removable from the drill guide of the patellar trial piece during a knee repair surgery.

6. The device of claim 5 wherein the plurality of pegs is selectable from pegs made of different materials.

7. The device of claim 5 wherein at least one of a moment of inertia and a center of gravity of the patella trial piece are adjustable to match that of the patient patella by selecting different pegs.

8. A system for repairing a patient patella, the patient patella having a moment of inertia and a center of gravity, the system comprising:
a plurality of variable weights comprising at least two pegs with different weights from each other; a patellar trial piece comprising an articular surface member, a drill guide, and an enclosure attached to a bottom surface of the drill guide, the patellar trial piece and the variable weights configured to be attached together through the drill guide, the enclosure configured to cover the attached variable weights, and the patellar trial piece configurable to correct at least one of the moment of inertia and the center of gravity of the trial piece to correspond to that of the patient patella to achieve optimal tracking and full range of motion; and a patellar implant with embedded weights, wherein the embedded weights correspond to the at least two pegs with different weights, and wherein a total weight of the patellar implant is in accordance with a combined mass of a shaved part of the patient patella.

9. The system of claim 8, wherein the patellar trial piece is converted to the patellar implant after a plurality of fixation pegs are fixed permanently to a bottom surface.

10. The system of claim 8, wherein the patellar implant adjusts a weight and a center of gravity of the patient patella to provide additional bearing to the patient patella to minimize tilting and any instability during patella motion.

11. The system of claim 8, wherein at least two of the plurality of variable weights have the same physical dimensions with different weights from each other.

12. The system of claim 8, wherein the enclosure covers the attached variable weights and the bottom surface of the drill guide.

* * * * *